United States Patent
Norton

(10) Patent No.: US 7,628,914 B2
(45) Date of Patent: Dec. 8, 2009

(54) METHODS FOR TIME-ALIGNMENT OF LIQUID CHROMATOGRAPHY-MASS SPECTROMETRY DATA

(75) Inventor: Scott M. Norton, Durham, NC (US)

(73) Assignee: PPD Biomarker Discovery Sciences, LLC, Menlo Park, CA (US)

( * ) Notice: Subject to any disclaimer, the term of this patent is extended or adjusted under 35 U.S.C. 154(b) by 786 days.

(21) Appl. No.: 11/339,235

(22) Filed: Jan. 24, 2006

(65) Prior Publication Data

US 2006/0131222 A1    Jun. 22, 2006

Related U.S. Application Data

(63) Continuation of application No. 10/435,581, filed on May 9, 2003, now Pat. No. 6,989,100.

(60) Provisional application No. 60/379,003, filed on May 9, 2002.

(51) Int. Cl.
*B01D 15/08* (2006.01)

(52) U.S. Cl. .................. 210/198.2; 210/656; 73/61.52; 250/282; 702/30

(58) Field of Classification Search ................ 210/635, 210/656, 198.2; 73/61.52; 250/282, 288; 702/30
See application file for complete search history.

(56) References Cited

U.S. PATENT DOCUMENTS

| | | | |
|---|---|---|---|
| 3,552,865 A | 1/1971 | Leung et al. |
| 3,690,836 A | 9/1972 | Buissiere et al. |
| 3,997,298 A | 12/1976 | McLafferty et al. |
| 3,999,047 A | 12/1976 | Green |
| 4,405,235 A | 9/1983 | Rossiter |
| 4,426,451 A | 1/1984 | Columbus |
| 4,643,570 A | 2/1987 | Machler et al. |
| 4,752,888 A | 6/1988 | Yoshihara |
| 4,761,381 A | 8/1988 | Blatt et al. |
| 4,786,813 A | 11/1988 | Svanberg et al. |
| 4,844,617 A | 7/1989 | Kelderman et al. |
| 4,963,498 A | 10/1990 | Hillman et al. |
| 5,072,382 A | 12/1991 | Kamentsky |
| 5,091,652 A | 2/1992 | Mathies et al. |
| 5,119,315 A | 6/1992 | Kemp et al. |
| 5,127,730 A | 7/1992 | Brelje et al. |
| 5,192,980 A | 3/1993 | Dixon et al. |
| 5,239,178 A | 8/1993 | Derndinger et al. |
| 5,274,240 A | 12/1993 | Mathies et al. |
| 5,304,810 A | 4/1994 | Amos |

(Continued)

FOREIGN PATENT DOCUMENTS

DE    19829094    1/2000

(Continued)

OTHER PUBLICATIONS

Aach & Church (2001) Bioinformatics 17:495-508.

(Continued)

*Primary Examiner*—Ernest G Therkorn
(74) *Attorney, Agent, or Firm*—Sheridan Ross P.C.

(57) ABSTRACT

Nonlinear retention time variations in chromatography-mass spectrometry data sets are adjusted by time-alignment methods, enabling automated comparison of spectra for differential phenotyping and other applications.

8 Claims, 11 Drawing Sheets

U.S. PATENT DOCUMENTS

| | | | |
|---|---|---|---|
| 5,377,003 A | 12/1994 | Lewis et al. |
| 5,412,208 A | 5/1995 | Covey et al. |
| 5,430,542 A | 7/1995 | Shepherd |
| 5,446,532 A | 8/1995 | Yamazaki |
| 5,453,505 A | 9/1995 | Lee et al. |
| 5,456,252 A | 10/1995 | Vari et al. |
| D366,938 S | 2/1996 | Shartle et al. |
| 5,492,833 A | 2/1996 | Rodriguez et al. |
| 5,523,573 A | 6/1996 | Hanninen et al. |
| 5,532,873 A | 7/1996 | Dixon |
| 5,547,849 A | 8/1996 | Baer et al. |
| 5,556,764 A | 9/1996 | Sizto et al. |
| 5,578,832 A | 11/1996 | Trulson et al. |
| 5,585,246 A | 12/1996 | Dubrow et al. |
| 5,592,402 A | 1/1997 | Beebe et al. |
| 5,627,041 A | 5/1997 | Shartle |
| D382,648 S | 8/1997 | Shartle et al. |
| 5,658,735 A | 8/1997 | Lee |
| D383,852 S | 9/1997 | Shartle et al. |
| 5,672,869 A | 9/1997 | Windig et al. |
| 5,682,038 A | 10/1997 | Hoffman |
| 5,687,964 A | 11/1997 | Stephan et al. |
| 5,689,110 A | 11/1997 | Dietz et al. |
| 5,692,220 A | 11/1997 | Diamond et al. |
| 5,710,713 A | 1/1998 | Wright et al. |
| D391,373 S | 2/1998 | Shartle |
| 5,713,364 A | 2/1998 | Debaryshe et al. |
| 5,726,751 A | 3/1998 | Altendorf et al. |
| 5,734,058 A | 3/1998 | Lee |
| 5,736,410 A | 4/1998 | Zarling et al. |
| 5,739,000 A | 4/1998 | Bierre et al. |
| 5,741,411 A | 4/1998 | Yeung et al. |
| D395,708 S | 6/1998 | Shartle |
| 5,795,729 A | 8/1998 | Lee |
| 5,814,820 A | 9/1998 | Dong et al. |
| 5,832,826 A | 11/1998 | Mack et al. |
| 5,867,610 A | 2/1999 | Lee et al. |
| 5,871,946 A | 2/1999 | Lucas et al. |
| 5,885,841 A | 3/1999 | Higgs, Jr. et al. |
| 5,910,287 A | 6/1999 | Cassin et al. |
| 5,912,134 A | 6/1999 | Shartle |
| 5,932,428 A | 8/1999 | Dubrow et al. |
| 5,962,238 A | 10/1999 | Sizto et al. |
| 5,981,180 A | 11/1999 | Chandler et al. |
| 5,995,989 A | 11/1999 | Gedcke et al. |
| 6,002,986 A | 12/1999 | Mito |
| 6,008,490 A | 12/1999 | Kato |
| 6,008,896 A | 12/1999 | Sabsabi et al. |
| 6,017,693 A | 1/2000 | Yates |
| 6,059,724 A | 5/2000 | Campbell et al. |
| 6,063,338 A | 5/2000 | Pham et al. |
| 6,066,216 A | 5/2000 | Ruppel, Jr. |
| 6,072,624 A | 6/2000 | Dixon et al. |
| 6,091,492 A | 7/2000 | Strickland et al. |
| 6,093,573 A | 7/2000 | Beamer et al. |
| 6,104,945 A | 8/2000 | Modell et al. |
| 6,112,161 A | 8/2000 | Dryden et al. |
| 6,133,046 A | 10/2000 | Clerc |
| 6,134,002 A | 10/2000 | Stimson et al. |
| 6,138,117 A | 10/2000 | Bayardo |
| 6,147,344 A | 11/2000 | Annis et al. |
| 6,200,532 B1 | 3/2001 | Wu et al. |
| 6,207,955 B1 | 3/2001 | Wells et al. |
| 6,215,892 B1 | 4/2001 | Douglass et al. |
| 6,229,603 B1 | 5/2001 | Coassin et al. |
| 6,229,635 B1 | 5/2001 | Wulf |
| 6,232,114 B1 | 5/2001 | Coassin et al. |
| 6,236,945 B1 | 5/2001 | Simpson et al. |
| 6,253,162 B1 | 6/2001 | Jarman et al. |
| 6,278,794 B1 | 8/2001 | Parekh et al. |
| 6,334,099 B1 | 12/2001 | Grace et al. |
| 6,376,843 B1 | 4/2002 | Palo |
| 6,377,842 B1 | 4/2002 | Pogue et al. |
| 6,388,788 B1 | 5/2002 | Harris et al. |
| 6,391,649 B1 | 5/2002 | Chait et al. |
| 6,400,487 B1 | 6/2002 | Harris et al. |
| 6,421,612 B1 | 7/2002 | Agrafiotis et al. |
| 6,449,584 B1 | 9/2002 | Bertrand et al. |
| 6,514,767 B1 | 2/2003 | Natan |
| 6,526,299 B2 | 2/2003 | Pickard |
| 6,552,784 B1 | 4/2003 | Dietz et al. |
| 6,590,204 B2 | 7/2003 | Baranov |
| 6,603,537 B1 | 8/2003 | Dietz et al. |
| 6,620,591 B1 | 9/2003 | Dunlay et al. |
| 6,625,546 B2 | 9/2003 | Sepetov et al. |
| 6,642,059 B2 | 11/2003 | Chait et al. |
| 6,646,271 B2 | 11/2003 | Yokokawa et al. |
| 6,687,395 B1 | 2/2004 | Dietz et al. |
| 6,753,966 B2 | 6/2004 | Von Rosenberg |
| 6,787,761 B2 | 9/2004 | Hastings |
| 6,800,860 B2 | 10/2004 | Dietz et al. |
| 6,835,927 B2 | 12/2004 | Becker et al. |
| 6,858,435 B2 | 2/2005 | Chervet et al. |
| 6,873,915 B2 | 3/2005 | Hastings |
| 6,937,330 B2 | 8/2005 | Dietz et al. |
| 6,950,185 B1 | 9/2005 | Da Silva et al. |
| 6,962,818 B2 | 11/2005 | Schneider et al. |
| 6,979,830 B2 | 12/2005 | Dietz et al. |
| 6,989,100 B2 | 1/2006 | Norton |
| 7,197,401 B2 | 3/2007 | Hastings |
| 2001/0019829 A1 | 9/2001 | Nelson et al. |
| 2002/0049152 A1 | 4/2002 | Nock et al. |
| 2002/0053545 A1 | 5/2002 | Greef |
| 2002/0095260 A1 | 7/2002 | Huyn |
| 2002/0095419 A1 | 7/2002 | Parce |
| 2002/0102610 A1 | 8/2002 | Townsend et al. |
| 2002/0123055 A1 | 9/2002 | Estell et al. |
| 2002/0141051 A1 | 10/2002 | Vogt et al. |
| 2003/0087322 A9 | 5/2003 | Aebersold et al. |
| 2004/0257576 A1 | 12/2004 | Kirsch et al. |
| 2006/0000984 A1 | 1/2006 | Wolleschensky et al. |

FOREIGN PATENT DOCUMENTS

| | | |
|---|---|---|
| EP | 0296136 | 12/1988 |
| EP | 0421736 | 4/1991 |
| EP | 0681177 | 11/1995 |
| EP | 0969283 A1 | 1/2000 |
| GB | 1407247 | 9/1975 |
| WO | WO - 97 43732 | 11/1997 |
| WO | WO 98/16661 | 4/1998 |
| WO | WO 00/67017 | 11/2000 |
| WO | WO - 00 70340 | 11/2000 |
| WO | WO 01/35266 | 5/2001 |
| WO | WO - 01 44269 | 6/2001 |
| WO | WO - 0288819 | 11/2002 |

OTHER PUBLICATIONS

Breen, et al. (2000) Electrophoresis 21:2243-2251.
Bryant et al. (2001) Rapid Commun. Mass Spectrom. 15:418-427.
Bylund et al. (2002) J. of Chromatography A. 961:237-244.
Chace (2001) Chem. Rev. 101:445-477.
Chelius et al. (2002) J. Proteome Res. 1:317-323.
do Lago et al. (1995) Anal. Chim. Acta, 310:281-288.
Fiehn et al. (2000) Nat. Biotech. 18:1157-1161.
Grung & Kvalheim (1995) Analytica Chimica Acta 304:57-66.
Gygi et al. (1999) Nat. Biotech. 17:994-999.
Hastings et al. (2002) Rapid Communications in Mass Spectrometry 16(5):462-467.
Kassidas et al. (1998) AIChE Journal 44(4):864-875.
Koradi et al. (1998) J. Mag. Res. 135:288-297.
Nielsen et al. (1998) J. of Chromatography A. 805:17-35.
Pravdova et al. (2002) Analytica Chimica Acta 456:77-92.
Prazen et al. (Jan. 15, 1998) Anal. Chem. 70:218-225.

Sakoe & Chiba (2002) IEEE Transactions on Acoustics, Speech and Signal Processing ASSP26(1):43-49.
Schoonjans et al. (2000) J. Pharm. & Biomed. Analysis 21:1197-1214.
Stein (1999) J. Am. Soc. Mass Spectrom. 10:770-81.
Wang et al. (1987) Analytical Chemistry 59:649-654.
Windig et al. (1996) Anal. Chem., 68:3602-3606.
International Search Report for International (PCT) Patent Application No. PCT/US03/14729, mailed Nov. 14, 2003.
Baumgarth et al., 2000, "A Practical Approach to Multicolor Flow Cytometry for Immunophenotyping," J. Immunol Methods, 243(1-2):77-97.
Beavis et al., 1996, "Allo-7: A New Fluorescent Tandem Dye for Use in Flow Cytometry," Cytometry 24(4)390-395.
Berlier et al., 2003, "Quantitative Comparison of Long-Wavelength Alexa Fluor Dyes to Cy Dyes: Fluorescence of the Dyes and Their Bioconjugates," J. Histochem Cytochem, 51(12):1699-1712.
Beu et al., 2004, "Broadband Phase Correction of FT-ICR Mass Spectra via Simultaneous Excitation and Detection," Anal. Chem., v. 76, pp. 5756-5761.
Bruchez et al., 1998, "Semiconductor Nanocrystals as Fluorescent Biological Labels," Science, 281(5385):2013-2016.
Bucknall et al., 2002, "Practical Quantitative Biomedical Applications of MALDI-TOF Mass Spectrometry", J. Am. Soc. Mass Spectrom. 13:1015.
Bylund, 2001, "Chemometric Tools for Enhanced Performance in Liquid Chromatography—Mass Spectrometry," Acta Univ. Ups., Comprehensive Summaries of Uppsala Dissertations from the Faculty of Science and Technology, 07. 47 pp. Uppsala. ISBN 91-554-4946-8.
Cagney et al., 2002, "De Novo Peptide Sequencing and Quantitative Profiling of Complex Protein Mixtures Using Mass-Coded Abundance Tagging", Nat. Biotech. 20:163.
Caprioli et al., 1972, "Use of Stable Isotopes", Biochem. Appl. Mass Spectrom. 27:735.
Coons, 1961, "The Beginnings of Immunofluorescence," J. Immunol, 87:499-503.
De Rosa et al., 2001, "11-Color, 13-Parameter Flow Cytometry: Identification of Human Naive T-Cells by Phenotype, Function, and T-cell Receptor Diversity," Nat. Med., 7(2):245-248.
De Rosa et al., 2003, "Beyond Six Colors: a New Era in Flow Cytometry," Nature Medicine, vol. 9, No. 1, pp. 112-117.
Dietz et al., 1996, "Volumetric Capillary Cytometry: A New Method for Absolute Cell Enumeration", Cytometry 23:177-186.
Elavathil et al., 1996, "Reproducibility of DNA Ploidy and S-Phase Values from Parraffin-Embedded Tissue", Analytical and Quantitative Cytology and Histology, vol. 18, No. 4, 316-322.
Felinger, 1998, "Data Analysis and Signal Processing In Chromatographpy," Data Handling in Science and Technology, vol. 21, pp. 149-152.
Glazer et al., 1983, "Fluorescent Tandem Phycobiliprotein Conjugates- Emission Wavelength Shifting by Energy Transfer," Biophys J, 43(3):383-386.
Ha et al., 1999, "Single-molecule Fluorescence Spectroscopy of Enzyme Conformational Dynamics and Cleavage Mechanism," Biophysics, vol. 96, pp. 893-898.
Hamberg et al.,1973, "Quantitative Studies on Prostaglandin Synthesis in Man", Anal. Biochem., 55:368.
Holst, 1998, "CCD Arrays, Camera and Displays", 2d Ed., JCD Publishing and SPIE Optical Engineering Press, pp. i-xxiii.
Jeanmaire et al., 1977, "Surface Raman Spectroelectrochemistry Part 1: Heterocyclic, Aromatic, and Aliphatic Amines Adsorbed on the Anodized Silver Electrode," J. Electroanal. Chem., 84:1-20.
Ji et al., 2000, "Strategy for Qualitative and Quantitative Analysis in Proteomics Based on Signature Peptides", J. Chromat, B 745:197.
Kamentsky, 2001, "Laser Scanning Cytometry," Methods Cell, Biol., 63:51-87.
Kantor et al., 1996, "FACS Analysis of Leukocytes," In: Herzenberg LA, Weir DM, Herzenberg LA, Blackwell C, editors, Weir's Handbook of Experimental Immunology, 5th ed. vol. 2. Cambridge, MA:Blackwell Science; p. 49.1-49.13
Kantor, 2002, "Comprehensive Phenotyping and Biological Marker Discovery," Disease Markers,18(2):91-97.
Kantor et al., 2004, "Immune Systems Biology: Immunoprofiling of Cells and Molecules," BioTechniques, 36(3):520-524.
Kantor et al., 2004, "Biomarker Discovery by Comprehensive Phenotyping for Autoimmune Diseases," Clinical Immunology, 111:186-195.
Kast et al., 2003, "Noise Filtering Techniques for Electrospray Quadrupole Time of Fluid Mass Spectra," J. Am. Soc. Mass Spectrom., v. 14, pp. 766-776.
Mahalingam, 1996, "Analysis of Surface Density of Expression of Molecules by Flow Cytometry", Cytometry 24:190.
Moore et al., 1993, "Median Filitering for Removal of Low-Frequency Background Drift," Anal.Chern 65:188-191.
Mujumdar et al., 1996, "Cyanine-Labeling Reagents: Sulfoindocyanine Succinimidyl Esters," Bioconjug Chem, 7, 356-362.
Nelson et al., 1995, "Mass Spectrometric Immunoassay", Anal. Chem. 67:1153.
Norton et al., 2000, "Cell Enumeration and Characterization in Microvolume Laser Scanning Cytometry; A Multicolor Image Processing Package," IBOS Society of Photo-Optical Instrumentation Engineers, p. 20-30.
Oda at al., 1999, "Accurate Quantitation of Protein Expression and Site-Specific Phosphorylation," Proc. Natl. Acad. Sci. USA 96:6591.
Oi et al., 1982, "Fluorescent Phycobiliprotein Conjugates for Analyses of Cells and Molecules," J. Cell Biol, 93(3):981-6.
Panchuk-Voloshina et al., 1999, "Alexa Dyes, A Series of New Fluorescent Dyes That Yield Exceptionally Bright, Photostable Conjugates," J. Histochem Cytochem, 47(9):1179-88.
Perez et al., 2002, "Simultaneous Measurement of Multiple Active Kinase States Using Polychromatic Flow Cytometry," Nat Biotechnol, 20(2):155-162.
Perez et al., 2004, "Flow Cytometric Analysis of Kinase Signaling Cascades," Methods Mol Biol, 263:67-94.
Perou et al., 2000, "Molecular Portraits of Human Breast Tumours", Nature, vol. 406, pp. 747-752.
Pinajian et al., 1953, "The Isotope Dilution Procedure of Analysis", J. Am. Phar. Assoc., 301-304.
Proceedings of SPIE V, 1997, "Ultrasensitive Biochemical Diagnostics II", The International Society for Optical Engineering, Feb. 10-12, San Jose, CA.
Roederer at al., 1996, "Cy7PE and Cy7APC: Bright New Probes for Immunofluorescence," Cytometry, 24(3):191-7.
Stewart et al., 1999, "Four Color Compensation", Cytometry, vol. 38, No. 4, 161-175.
Van Duyne, 1979, "Laser Excitation of Raman Scattering from Adsorbed Molecules on Electrode Surfaces," In: Moore CB, editor, Chemical and Biochemical Applications of Lasers, pp. 101-185.
Voyksner et al., 1999, "Investigating the use of an Octupole Ion Guide for Ion Storage and High-pass Mass Filtering to Improve the Quatitative Performance of Electro spray Ion Trap Mass Spectrometry," Rapid Commun. Mass Spectrom., v. 13, pp, 1427-1437.
Waggoner at al., 1993, "PE-CY5- A New Fluorescent Antibody Label for Three-color Flow Cytometry with a Single Laser," Ann N Y Acad Sci, 677:185-93.
Walton at al., 2000, "Microvolume Laser Scanning Cytometry Platform for Biological Marker Discovery," Proc.SPIE-Int.Soc.Opt. Eng., 3926:192-201.
Wang et al., 2003, "Quantification of Proteins and Metabolites by Mass Spectrometry Without Isotopic Labeling or Spiked Standards", Anal, Chem. 75:4818.
Watson et al., 2003, "Lighting up Cells with Quantum Dots," Biotechniques, 34(2):296-300, 302-3.
Wu et al., 2003, "Immunofluorescent Labeling of Cancer Marker Her2 and Other Cellular Targets with Semiconductor Quantum Dots," Nat Biotechnol, 21(1):41-6.
Zuck at al., 1999, "Ligand-receptor Binding Measured by Laser-scanning Imaging," Proc. Natl. Acad. Sci., 96(20)11122-11127.
Constantino, et al., 2001 "Single-Molecule Detection Using Surface-Enhanced Resonance Raman Scattering and Langmuir—Blodgett Monolayers," Anal. Chem., vol. 73, pp, 3674-3678.
Doering et al., 2002, "Single-Molecule and Single-Nanoparticle SERS: Examining the Roles of Surface Active Sites and Chemical Enhancement," *J. Phys. Chem. B.*, 106:311-317.

Ha, T., 2001, "Single-Molecule Fluorescence Resonance Energy Transfer," *Methods*, 25:78-86.

Kneipp et al., 1997, "Single Molecule Detection Using Surface-Enhanced Raman Scattering (SERS)," *Physical Review Letters*, 78(9):1667-1670.

Kneipp et al., 1999, "Ultrasensitive Chemical Analysis by Raman Spectroscopy," *Chem. Rev.*, 99:2957-2975.

Martens et al., 1999, "A Generic Particle-Based Nonradioactive Homogeneous Multiplex Method for High-Throughput Screening Using Microvolume Fluorimetry," *Analytical Biochemistry*, 273:20-31.

Mulvaney, et al., 2000 "Raman Spectroscopy," Proc. Anal. Chem., vol. 72, pp. 145R-157R.

Mulvaney et al., 2003, "Glass-Coated, Analyte-Tagged Nanoparticles: A New Tagging System Based on Detection with Surface-Enhanced Raman Scattering," *Langmuir*; 19:4784-4790.

Nie et al., 1997, "Probing Single Molecules and Single Nanoparticles by Surface-Enhanced Raman Scattering," Science, New Series, 275(5303):1102-1106.

Rossetti et al., 1982, "Electron-Hole Recombination Emission as a Probe of Surface Chemistry in Aqueous CdS Colloids," *J. Phys. Chem.*, 86:4470-4472.

Steigerwald et al., 1988, "Surface Derivatization and Isolation of Semiconductor Cluster Molecules," *J. Am. Chem. Soc.*, 110:3046-3050.

Swartzman et al., 1999, "A Homogeneous and Multiplexed Immunoassay for High-Throughput Screening Using Fluorometric Microvolume Assay Technology," *Analytical Biochemistry*, 271:143-151.

Tibbe et al., 1999, "Optical Tracking and Detection of Immunomagnetically Selected and Aligned Cells," *Nature Biotechnology*, 17:1210-1213.

Wyant et al., 2001, "Whole Blood Microvolume Laser Scanning Cytometry for Monitoring Resting and Activated Platelets," *Platelets*, 12:309-318.

| $t_{ref}$ | $t_{test}$ |
|---|---|
| 1 | 1 |
| 2 | 2 |
| ⋮ | ⋮ |
| 26 | 21 |
| 27 | 22 |
| 28 | 24 |
| ⋮ | ⋮ |
| 41 | 41 |
| 42 | 42 |
| 43 | 43 |
| ⋮ | ⋮ |
| 71 | 76 |
| 72 | 77 |
| 73 | 78 |
| ⋮ | ⋮ |
| 98 | 98 |
| 99 | 99 |
| 100 | 100 |

FIG. 4B

| Reference Peak List | | Test Peak List | |
|---|---|---|---|
| Mass(au) | Time(min) | Mass(au) | Time(min) |
| 456.3 | 23.4 | 451.2 | 54.8 |
| 457.4 | 32.5 | 462.9 | 14.0 |
| 457.8 | 12.8 | 463.2 | 11.2 |
| 463.1 | 11.8 | 463.5 | 9.8 |
| 467.7 | 54.3 | 473.2 | 34.3 |
| 469.8 | 44.1 | 482.1 | 27.5 |

US 7,628,914 B2

METHODS FOR TIME-ALIGNMENT OF LIQUID CHROMATOGRAPHY-MASS SPECTROMETRY DATA

CROSS-REFERENCE TO RELATED APPLICATIONS

This application is a continuation of U.S. patent application Ser. No. 10/435,581, filed May 9, 2003, now U.S. Pat. No. 6,989,100, which claims the benefit of U.S. Provisional Application No. 60/379,003, "Methods for Time-Aligning of Liquid Chromatography-Mass Spectrometry Data for Differential Phenotyping," filed May 9, 2002, which is incorporated herein by reference.

FIELD OF THE INVENTION

The present invention relates generally to analysis of data collected by analytical techniques such as chromatography and spectrometry. More particularly, it relates to methods for time-aligning multi-dimensional chromatograms of different samples to enable automated comparison among sample data.

BACKGROUND OF THE INVENTION

The high sensitivity and resolution of liquid chromatography-mass spectrometry (LC-MS) make it an ideal tool for comprehensive analysis of complex biological samples. Comparing spectra obtained from samples corresponding to different patient cohorts (e.g., diseased versus non-diseased, or drug responders versus non-responders) or subjected to different stimuli (e.g., drug administration regimens) can yield valuable information about sample components correlated with particular conditions. Such components may serve as biological markers that enable earlier and more precise diagnosis, patient stratification, or prediction of clinical outcomes. They may also guide the discovery of suitable and novel drug targets. Because this approach extracts a large amount of information from a very small sample size, automated data collection and analysis methods are desirable.

LC-MS data are reported as intensity or abundance of ions of varying mass-to-charge ratio (m/z) at varying chromatographic retention times. A two-dimensional spectrum of LC-MS data from a single sample is shown in FIG. 1, in which the darkness of points corresponds to signal intensity. A horizontal slice of the spectrum yields a mass chromatogram, the abundance of ions in a particular m/z range as a function of retention time. A vertical slice is a mass spectrum, a plot of abundance of ions of varying m/z at a particular retention time interval. The two-dimensional data are acquired by performing a mass scan at regular intervals of retention time. Summing the mass spectrum at each retention time yields a total ion chromatogram (TIC), the abundance of all ions as a function of retention time. Local maxima in intensity (with respect to both retention time and m/z) are referred to as peaks. In general, peaks may span several retention time scan intervals and m/z values.

One significant obstacle for automated analysis of LC-MS data is the nonlinear variability of chromatographic retention times, which can exceed the width of peaks along the retention time axis substantially. This variability arises from, for example, changes in column chemistry over time, instrument drift, interactions among sample components, protein modifications, and minor changes in mobile phase composition. While constant time offsets can be corrected for easily, nonlinear variations are more problematic and significantly hamper the recognition of corresponding peaks across sample spectra. This problem is illustrated by the chromatograms of FIG. 2, in which the dotted and solid curves represent total ion chromatograms of samples from two different patients. While it can be assumed that the dotted curve has been time-shifted from the solid curve, it is difficult to predict from the two curves to which of the two solid peaks the dotted peak corresponds.

Various methods have been provided in the art for addressing the problem of chromatographic retention time shifts, including correlation, curve fitting, and dynamic programming methods such as dynamic time warping and correlation optimized warping. For example, a time warping algorithm is applied to gas chromatography/Fourier transform infrared (FT-IR)/mass spectrometry data from a gasoline sample in C. P. Wang and T. L. Isenhour, "Time-warping algorithm applied to chromatographic peak matching gas chromatography/Fourier transform infrared/mass spectrometry," Anal. Chem. 59: 649-654, 1987. In this method, a single FT-IR interferogram is aligned with a TIC. While this method may be effective for simple samples, it may be inadequate for more complex samples such as biological fluids, which can contain thousands of different proteins and peptides, yielding thousands of potentially relevant and, more importantly, densely spaced (in both m/z and retention time) peaks.

There is still a need, therefore, for a robust method for time-aligning chromatographic-mass spectrometric data.

BRIEF DESCRIPTION OF THE FIGURES

FIGS. 4A-4B illustrate aspects of a dynamic time warping (DTW) method according to one embodiment of the present invention.

DETAILED DESCRIPTION OF THE INVENTION

Figure 1:
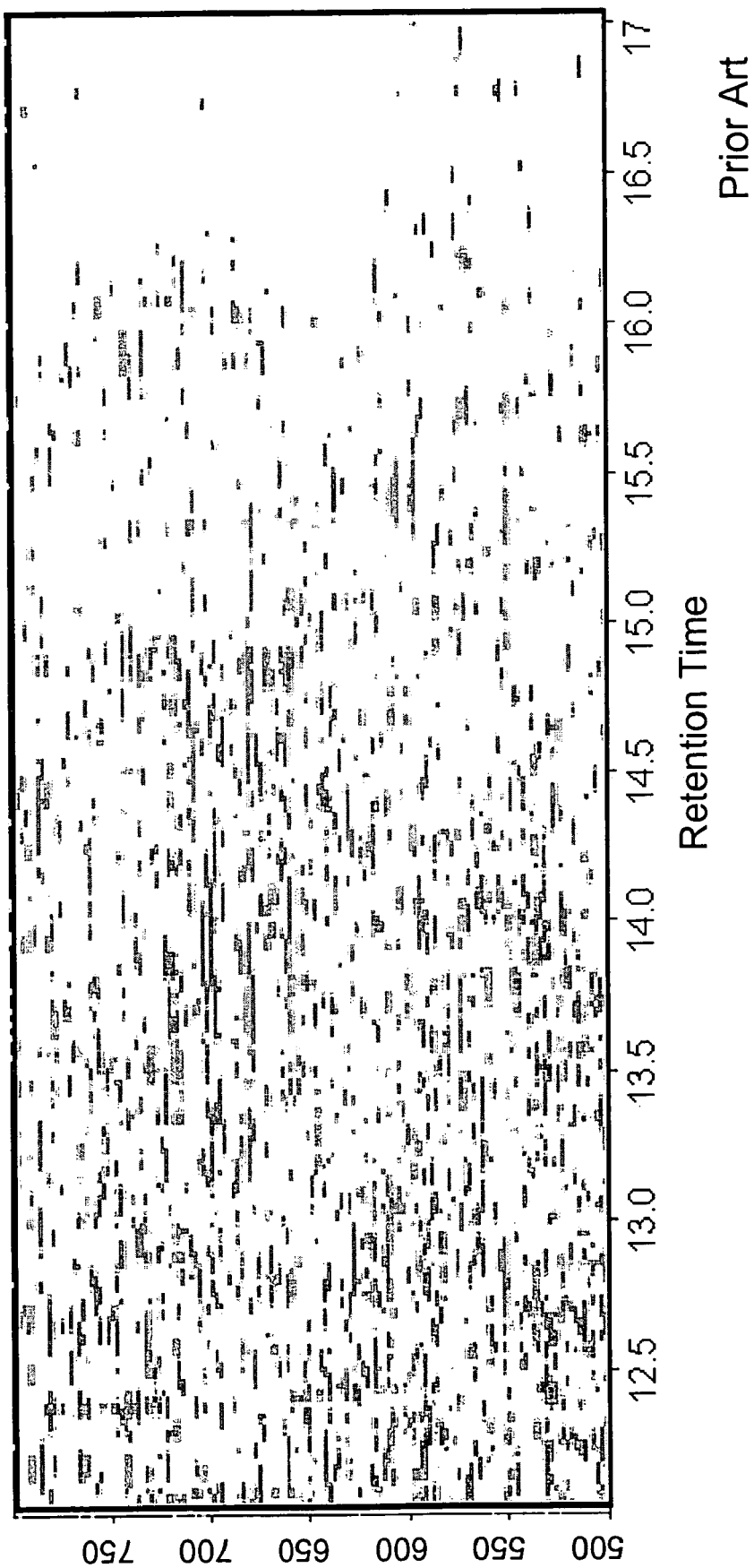
FIG. 1 (prior art) shows a sample two-dimensional liquid chromatography-mass spectrometry (LC-MS) data set.
Figure 2:
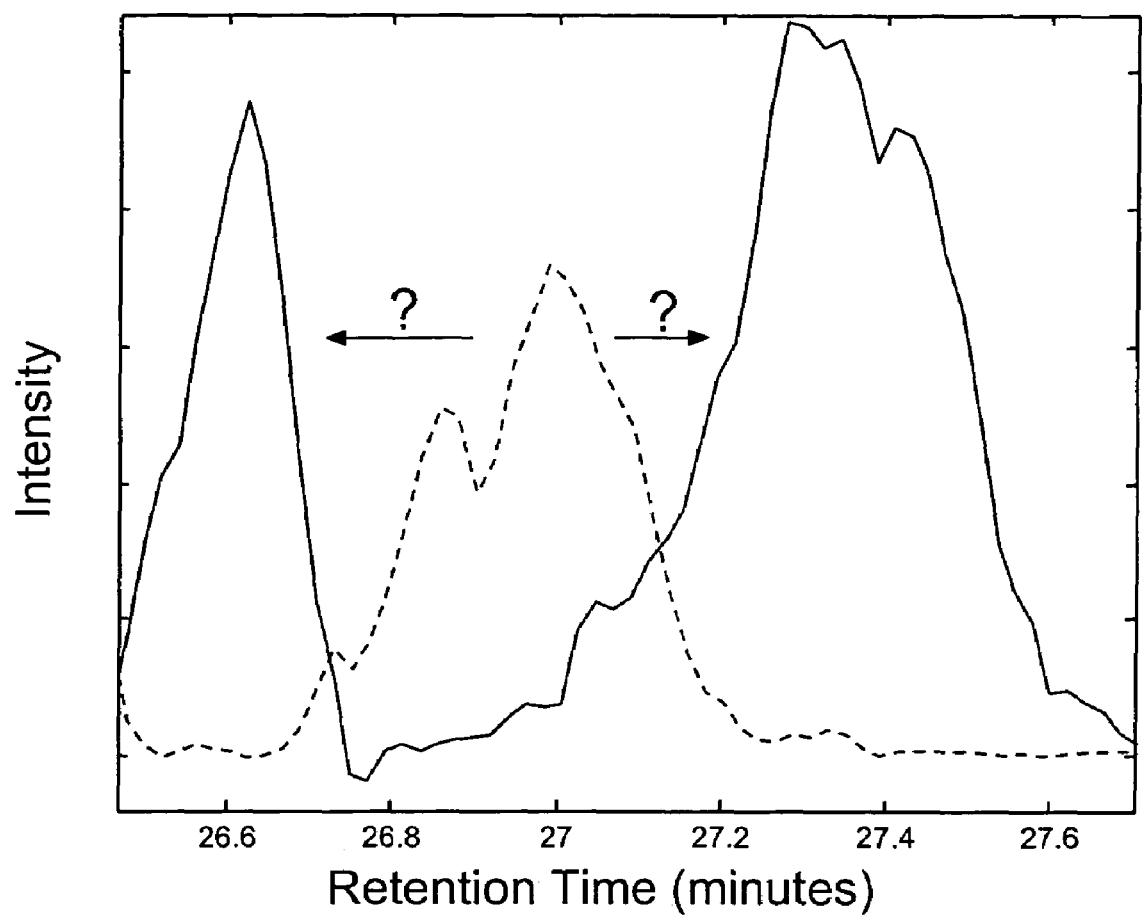
FIG. 2 is a schematic diagram of portions of total ion chromatograms of two different samples, illustrating the difficulties in properly time-aligning spectra.

Various embodiments of the present invention provide methods for time-aligning two-dimensional chromatography-mass spectrometry data sets, such as liquid chromatography-mass spectrometry (LC-MS) data sets, also referred to as spectra. These data sets can have nonlinear variations in retention time, so that corresponding peaks (i.e., peaks representing the same analyte) in different samples elute from the chromatographic column at different times. Additional embodiments provide methods for comparing samples and data sets, methods for identifying biological markers (biomarkers), aligned spectra produced according to these methods, samples compared according to these methods, biomarkers identified according to these methods, and methods for using the identified biomarkers for diagnostic and therapeutic applications.

The methods are effective at aligning two-dimensional data sets obtained from both simple and complex samples. Although complex and simple are relative terms and are not intended to limit the scope of the present invention in any way, complex samples typically have many more and more densely spaced spectral peaks than do simple samples. For examples, complex samples such as biological samples may have upwards of hundreds or thousands of peaks in sixty minutes of retention time, such that the total ion chromatogram (TIC) is too complex to allow resolution of individual features. Rather than use composite one-dimensional data such as the TIC, the methods in embodiments of the present invention use data from individual mass chromatograms, i.e., data representing abundances or intensities of ions in particular m/z ranges at particular retention times. The m/z range included within a single mass chromatogram may reflect the instrument precision or may be the result of preprocessing (e.g., binning) of the raw data, and is typically on the order of between about 0.1 and 1.0 atomic mass unit (amu). Mass scans typically occur at intervals of between about one and about three seconds.

In some embodiments of the present invention, computations are referred to as being performed "in dependence on at least two mass chromatograms from each data set." This phrase is to be understood as referring to computations on individual data from a mass chromatogram, rather than to data summed over a number of chromatograms.

While embodiments of the invention are described below with reference to chromatography and mass spectrometry, and particularly to liquid chromatography, it will be apparent to one of skill in the art how to apply the methods to any other hyphenated chromatographic technique. For example, the second dimension may be any type of electromagnetic spectroscopy such as microwave, far infrared, infrared, Raman or resonance Raman, visible, ultraviolet, far ultraviolet, vacuum ultraviolet, x-ray, or ultraviolet fluorescence or phosphorescence; any magnetic resonance spectroscopy, such as nuclear magnetic resonance (NMR) or electron paramagnetic resonance (EPR); and any type of mass spectrometry, including ionization methods such as electron impact, chemical, thermospray, electrospray, matrix assisted laser desorption, and inductively coupled plasma ionization, and any detection methods, including sector, quadrupole, ion trap, time of flight, and Fourier transform detection.

Time-alignment methods are applied to data sets acquired by performing chromatographic and spectrometric or spectroscopic methods on chemical or biological samples. The samples can be in any homogeneous or heterogeneous form that is compatible with the chromatographic instrument, for example, one or more of a gas, liquid, solid, gel, or liquid crystal. Biological samples that can be analyzed by embodiments of the present invention include, without limitation, whole organisms; parts of organisms (e.g., tissue samples); tissue homogenates, extracts, infusions, suspensions, excretions, secretions, or emissions; administered and recovered material; and culture supernatants. Examples of biological fluids include, without limitation, whole blood, blood plasma, blood serum, urine, bile, cerebrospinal fluid, milk, saliva, mucus, sweat, gastric juice, pancreatic juice, seminal fluid, prostatic fluid, sputum, broncheoalveolar lavage, and synovial fluid, and any cell suspensions, extracts, or concentrates of these fluids. Non-biological samples include air, water, liquids from manufacturing wastes or processes, foods, and the like. Samples may be correlated with particular subjects, cohorts, conditions, time points, or any other suitable descriptor or category.

Figure 3:
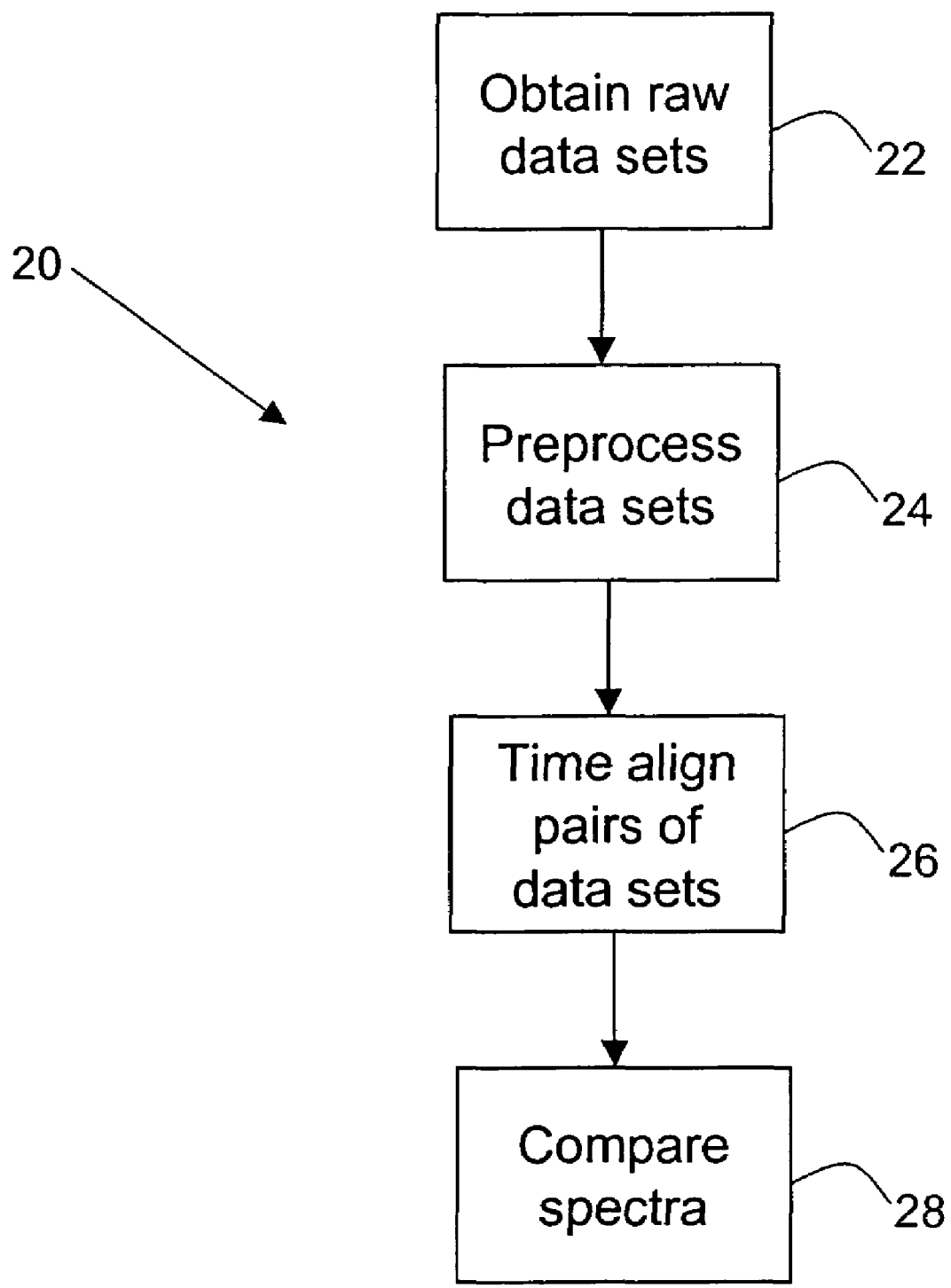
FIG. 3 is a flow diagram of one embodiment of the present invention, a method for comparing samples.

FIG. 3 is a flow diagram of a general method 20 according to one embodiment of the present invention. The method is typically implemented in software by a computer system in communication with an analytical instrument such as a liquid chromatography-mass spectrometry (LC-MS) instrument. In a first step 22, raw data sets are obtained, e.g., from the instrument, from a different computer system, or from a data storage device. The data sets, which are also referred to as spectra or two-dimensional data sets or spectra, contain intensity values for discrete values (or ranges of values) of chromatographic retention time (or scan index) and mass-to-charge ratio (m/z). At each scan time of the instrument, an entire mass spectrum is obtained, and the collection of mass spectra for the chromatographic run of that sample makes up the data set. Typically, a collection of data sets is acquired from a large number (i.e., more than two) of samples before subsequent processing occurs.

In an optional next step 24, the data sets are preprocessed using conventional algorithms. Examples of preprocessing techniques applied include, without limitation, baseline subtraction, smoothing, noise reduction, de-isotoping, normalization, and peak list creation. Additionally, the data can be binned into defined m/z intervals to create mass chromatograms. Data are collected at discrete scan times, but m/z values in the mass spectra are typically of very high mass precision. In order to create mass chromatograms, data falling within a specified m/z interval (e.g., 0.5 amu) are combined into a composite value for that interval. Any suitable binning algorithm may be employed; as is known in the art, the selection of a binning algorithm and its parameters may have implications for data smoothness, fidelity, and quality.

In step 26, a time-aligning algorithm is applied to one or more pair of data sets. One data set can be chosen (arbitrarily or according to a criterion) to serve as a reference spectrum and all other data sets time-aligned to this spectrum. For example, assuming the samples are analyzed on the instrument consecutively, the reference data set can correspond to the sample analyzed in the middle of the process. Alternatively, a feedback method can be implemented in which the degree of time shift is measured for each data set, potentially with respect to one or more of the data sets chosen arbitrarily as a reference data set, and the one with a median time shift, according to some metric, selected as the reference data set. Data sets can also be evaluated by a perceived or actual quality metric to determine which to select as the reference data set.

After the data sets are aligned to a common retention time scale, the aligned data sets can be compared automatically in step 28 to locate features that differentiate the spectra. For example, a peak that occurs in only certain spectra or at significantly different intensity levels in different spectra may represent a biological marker or a component of a biological marker that is indicative of or diagnostic for a characteristic of the relevant samples (e.g., disease, response to therapy, patient group, disease progression). If desired, the identity of the ions responsible for the distinguishing features can be identified. Biological markers may also be more complex combinations of spectral features or sample components with or without other clinical or biological factors. Identifying spectral differences and biological markers is a multi-step process and will not be described in detail herein. For more information, see U.S. patent application Ser. No. 09/994,576, "Methods for Efficiently Mining Broad Data Sets for Biological Markers," filed Nov. 27, 2001, which is incorporated herein by reference. In general, this step 28 is referred to as differential phenotyping, because differences among phenotypes, as represented by the comprehensive (rather than selective) LC-MS spectrum of expressed proteins and small molecules, are detected.

Step 26, time-aligning pairs of spectra, can be implemented in many different ways. In one embodiment of the invention, spectra are aligned using a variation of a dynamic time warping (DTW) method. DTW is a dynamic programming technique that was developed in the field of speech recognition for time-aligning speech patterns and is described in H. Sakoe and S. Chiba, "Dynamic programming algorithm optimization for spoken word recognition," *IEEE Trans. Acoust., Speech, Signal Process.* ASSP-26: 43-49, 1978, which is incorporated herein by reference.

In embodiments of the present invention, DTW aligns two data sets by nonlinearly stretching and contracting ("warping") the time component of the data sets to synchronize spectral features and yield a minimum distance between the two spectra. In asymmetric DTW, a test data set is warped to align with a reference data set. Alternatively, in symmetric DTW, both data sets are adjusted to fit a common time index. The following description is of asymmetric warping, but it will be apparent to one of ordinary skill in the art, upon reading this description, how to perform the analogous symmetric warping.

Figure 4A:
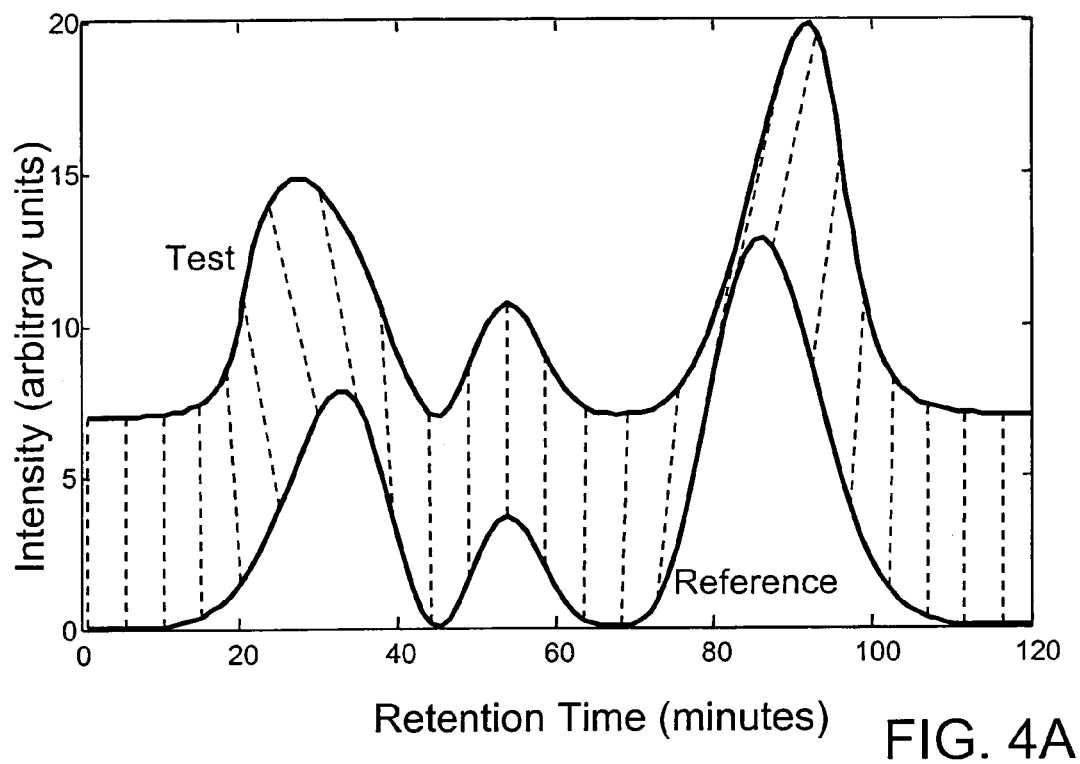

FIG. 4A is a plot of two chromatograms, labeled test and reference, whose time scales are nonlinearly related. That is, peaks representing identical analytes, referred to as corresponding peaks (and the corresponding points that make up these peaks), occur at different retention times, and there is no linear transformation of time components that will map corresponding peaks to the same retention times. Although the data are shown as continuous curves, each data set consists of discrete values (an entire mass spectrum) at a sequence of time indices; for clarity, only a single intensity value, rather than an entire mass spectrum, is shown at each time point. In the figure, corresponding points are connected by dashed lines, which represent a mapping of time points in the reference data set to time points in the test data set. This mapping is shown more explicitly in the table of FIG. 4B. The object of a DTW algorithm is to identify this time point mapping, from which an aligned reference data set may be constructed. Note that DTW aligns the entire data set, and not just peaks of the data set, and that DTW yields a discrete time point mapping, rather than a function that transforms the original time points into aligned time points. As a result, some points (reference and test) do not get mapped, and unmapped points can be handled as described below.

Conceptually, the DTW method considers a set of possible time point mappings and identifies the mapping that minimizes an accumulated distance function between the reference and test data sets. Consider the grid in FIG. 5, in which rows correspond to I time indices i in the test data set and columns to J time indices j in the reference data set (I and J can be different). Each possible time point mapping can be represented as a route c(k) through this grid, where c(k)=[i(k), j(k)] and $1 \leq k \leq K$. For example, if the test and reference data sets were perfectly aligned, the route would be a diagonal beginning in the upper left cell and proceeding to the lower right cell of the grid. The selected route represents the optimal time point mapping.

Figure 6A:
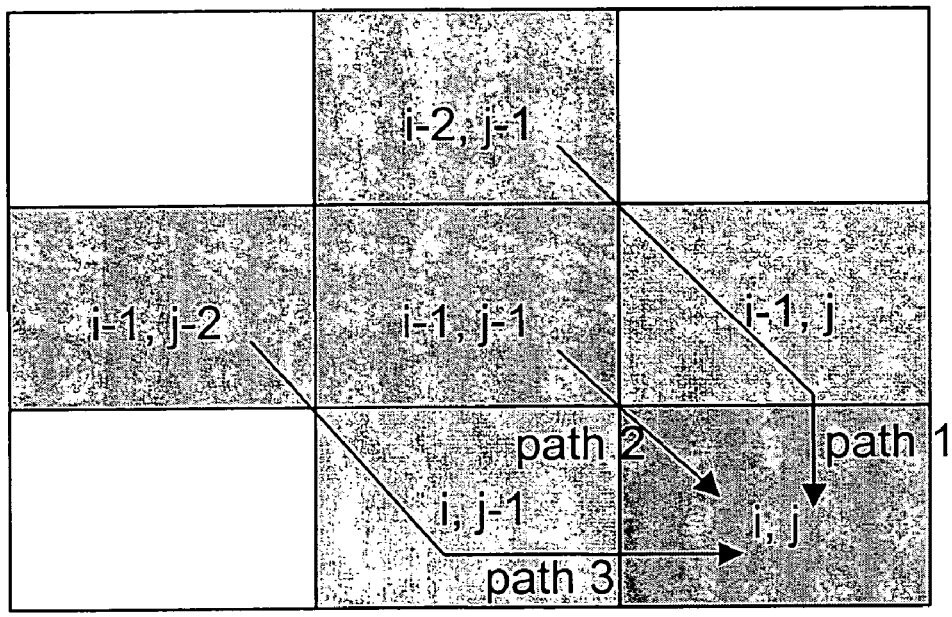
FIGS. 6A-6B illustrate two constraints on a DTW method according to one embodiment of the present invention.
Figure 6B:
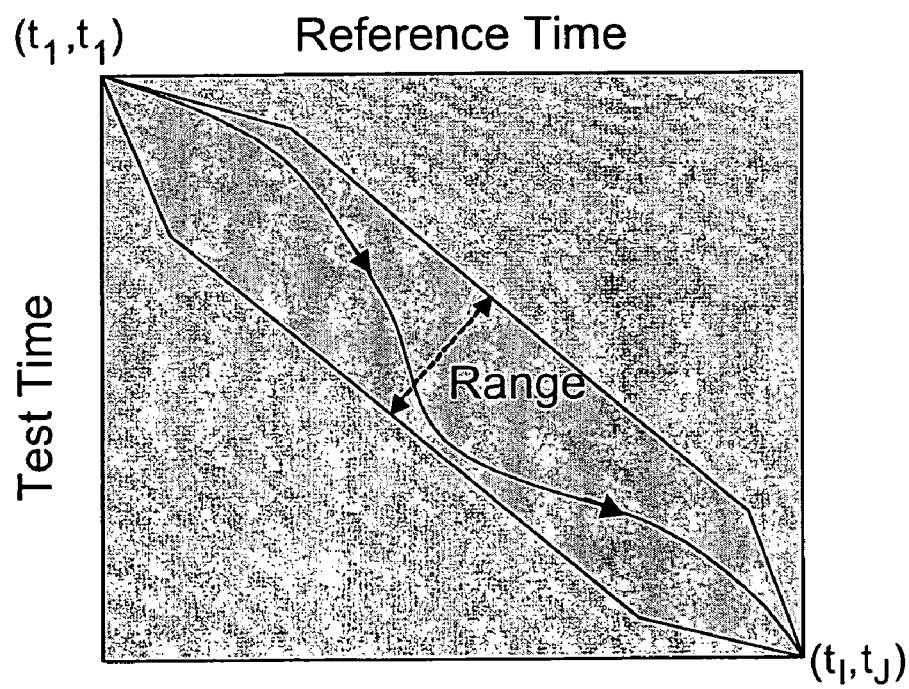

The set of possible routes is limited by three types of constraints: endpoint constraints; a local continuity constraint, which defines local features of the path; and a global constraint, which defines the allowable search space for the path. The endpoint constraint equates the first and last time point in each data set. In the grid, the upper left and lower right cells are fixed as the start and end of the path, respectively, i.e., c(1)=[1, 1] and c(K)=[I, J]. The local continuity constraint forces the path to be monotonic with a non-negative slope, meaning that, for a path c(k)=[i(k), j(k)], $i(k+1) \geq i(k)$ and $j(k+1) \geq j(k)$. This condition maintains the order of time points. An upper bound can also be placed on the slope to prevent excessive compression or expansion of time scales. The result of these conditions is that the path to an individual cell is limited to one of the three illustrated in FIG. 6A. Finally, the global constraint limits the path to a specified number of grid places from the diagonal, illustrated schematically in FIG. 6B. This latter constraints confines the solution to one that is physically realizable while also substantially limiting the computation time.

Figure 5:
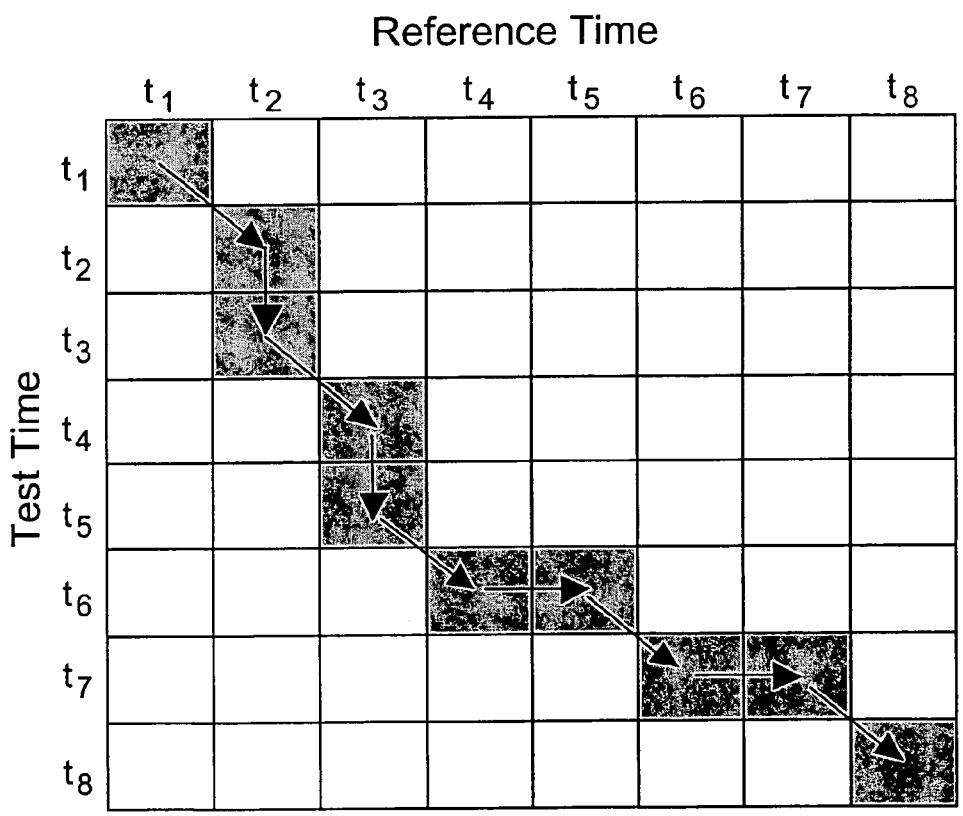
FIG. 5 shows a grid of chromatographic time points, used in DTW, with an optimal route through the grid indicated.

The optimal path through the grid is one that minimizes the accumulated distance function between the test and reference data sets over the route. Each cell [i, j] has an associated distance function between data sets at the particular i and j time indices. The distance function can take a variety of different forms. If only a single chromatogram (e.g., the TIC) were considered, the distance function $d_{i,j}$ between points $t_j^{ref}$ and $t_i^{test}$ would be:

$$d_{i,j} = (I_j^{ref} - I_i^{test})^2, \qquad (1)$$

where $I_j^{ref}$ is the $j^{th}$ intensity value of the reference spectrum and $I_i^{test}$ is the $i^{th}$ intensity value of the test spectrum. In embodiments of the present invention, however, M mass chromatograms of each data set are considered in computing the distance function, where $M \geq 2$, and so, in one embodiment, the distance function is:

$$d_{i,j} = \sum_{k=1}^{M} (I_{kj}^{ref} - I_{ki}^{test})^2, \qquad (2)$$

where $I_{kj}^{ref}$ is the $j^{th}$ intensity value of the $k^{th}$ reference chromatogram and $I_{ki}^{test}$ is the $i^{th}$ intensity value of the $k^{th}$ test chromatogram. Both $k^{th}$ chromatograms are for a single m/z range. Each cell of the grid in FIG. 5 is filled with the appropriate value of the distance function, and a route is chosen through the matrix that minimizes the accumulated distance function obtained by summing the values in each cell traversed, subject to the above-described constraints. Note that the two terms distance and route are not related; the distance refers to a metric of the dissimilarity between data sets, while the route refers to a path through the grid and has no relevant distance.

The route-finding problem can be addressed using a dynamic programming approach, in which the larger optimization problem is reduced to a series of local problems. At each allowable cell in the grid (FIG. 6B), the optimal one of the three (FIG. 6A) single-step paths is identified. After all cells have been considered, a globally optimal route is reconstructed by stepping backwards through the grid from the last cell. For more information on dynamic programming, see T. H. Cormen et al., *Introduction to Algorithms* ($2^{nd}$ ed.), Cambridge: MIT Press (2001), which is incorporated herein by reference.

Locally optimal paths are selected by minimizing the accumulated distance from the initial cell to the current cell. For the three potential single-step paths to the cell [i,j], the accumulated distances are:

$$D_{i,j}^{(1)} = D_{i-2,j-1} + 2d_{i-1,j} + d_{i,j}$$

$$D_{i,j}^{(2)} = D_{i-1,j-1} + 2d_{i,j},$$

$$D_{i,j}^{(3)} + D_{i-1,j-2} + 2d_{i,j-1} + d_{i,j} \qquad (3)$$

where $D_{i,j}^{(p)}$ represents the accumulated distance from $[1, 1]$ to $[i, j]$ when path p is traversed, $d_{i,j}$ is computed from equation (2), and $D_{i-1,j-1}$, $D_{i-2,j-1}$, and $D_{i-1,j-2}$ are evaluated in previous steps. The coefficient 2 is a weighting factor that inclines the path to follow the diagonal. It may take on other values as desired. The minimized accumulated distance for the cell $[i,j]$ is given by:

$$D_{i,j} = \min_p \left( D_{i,j}^{(p)} \right). \qquad (4)$$

This value is stored in an accumulated distance matrix for use in subsequent calculations, and the selected value of p is stored in an index matrix.

The dynamic programming algorithm proceeds by stepping through each cell and finding and storing the minimum accumulated distances and optimal indices. Typically the process begins at the top left cell of the grid and moves down through all allowed cells before moving to the next column, with the allowable cells in each column defined by the global search space. After the final cell has been computed, the optimal route is found by traversing the grid backwards to the starting cell [1, 1] based on optimal paths stored in the index matrix. Note that the route cannot be constructed in the forward direction, because it is not known until subsequent calculations whether the current cell will lie on the optimal route. Once the optimal route has been determined, an aligned test data set can be constructed.

Unless the test and reference data sets are perfectly aligned, there are points in both sets that do not get mapped. When the test time scale is compressed, some intermediate test points do not get mapped. These points are discarded. When the test time scale is expanded, there are reference time points for which no corresponding test point exists. Values of the points can be estimated, e.g., by linearly interpolating between intensity values of surrounding points that have been mapped to reference points.

The above-described methods and steps can be varied in many ways without departing from the scope of the invention. For example, alternative constraints can be applied to the route (e.g., different allowable local slopes, end points not fixed but rather constrained to allowable regions, different global search space), and alternative distance functions can be employed. The weighting factors for local paths can be varied from the value 2 used in equations (3). Additionally, a normalization factor can be included in the distance function. The distance function above is based on intensity, but, depending on how the data set is represented, can be based on any other coefficient of features of the data set. For example, the function can be computed from coefficients of wavelets, peaks, or derivatives by which the data set is represented. In this case, the distance is a measure of the degree of alignment of these features.

In the equations above, the distance function is computed based on data from M individual mass chromatograms. Any value of M is within the scope of the present invention, as are any selection criteria by which chromatograms are selected for inclusion. Reducing the number of chromatograms from the total number in the data set (e.g., 2000) to M can decrease the computation time substantially. Additionally, excluding noisy chromatograms or those without peaks can improve the alignment accuracy. There is generally an optimal range of M that balances alignment accuracy and computation time, and it is beneficial to choose a value of M in the lower end of the range, i.e., a value that minimizes computation time without sacrificing substantially the accuracy of time-alignment. It is also beneficial to include chromatograms containing peaks throughout the range of retention time; this is particularly important near the beginning and end of the chromatographic run, when there are fewer peaks. In one embodiment, between about 200 and about 400 chromatograms are used. Alternatively, between about 200 and about 300 chromatograms are used. In another embodiment, M is about 200.

A variety of selection criteria can be applied individually or jointly to select the chromatograms with which the distance function is computed. The selection criteria or their parameters (e.g., intensity thresholds) can be predetermined, computed at run time, or selected by a user. M can be a selected value (manually or automatically) or the result of applying the criterion or criteria (i.e., M chromatograms happen to fit the criteria).

One selection criterion is that a mass chromatogram have peaks in both the reference and test data sets, as determined by a manual or automated peak selection algorithm. Peak selection algorithms typically apply an intensity threshold and identify local maxima exceeding the threshold as peaks. The peaks may or may not be required to be corresponding (in m/z and retention time) for the chromatogram to meet the criterion. If corresponding peaks are required, a relatively large window in retention time is applied to account for the to-be-corrected retention time shifts.

Another selection criterion is that maximum, median, or average intensity values in a mass chromatogram exceed a specified intensity threshold, or that a single peak intensity or maximum, median, or average peak intensity values in the chromatogram exceed an intensity threshold. Alternatively, at least one individual peak intensity or the maximum, median, or average peak intensity can be required to fall between upper and lower intensity level thresholds. Another selection criterion is that the number of peaks in a mass chromatogram exceed a threshold value. These criteria are typically applicable to both the reference and test mass chromatograms.

When the selection criterion involves an intensity threshold, the threshold can be constant or vary with retention time to accommodate variations in mean or median signal intensity throughout a chromatographic run. Often, the beginning and end of the run yields fewer and lower intensity peaks than occur in the middle of the run, and lower thresholds may be suitable for these regions.

According to an alternative selection criterion, a set of the most orthogonal chromatograms is selected, i.e., the set that provides the most information. When an analyte is present in chromatograms of adjacent m/z values, these chromatograms may be redundant, providing no more information than is provided by a single chromatogram. Standard correlation methods can be applied to select orthogonal chromatograms. The orthogonal chromatograms are selected to span the elution time range, so that just enough information is provided to align the data sets accurately throughout the entire range. In this case, the selection criterion contains an orthogonality metric and a retention time range.

Individual selection criteria may be combined in many different ways. For example, in one composite selection criterion, peaks are first selected in the reference and test data sets using any suitable manual or automatic peak selection method. Next, a filter is applied separately to the two data sets to yield two subsets of peaks. This filter can be a single threshold or two (upper and lower) thresholds. A lower threshold ensures that peaks are above the noise level, while an upper threshold excludes falsely elevated values reflecting a saturated instrument detector. Corresponding peaks are then selected that appear in both the test and reference peak subsets. Chromatograms corresponding to these peaks are included in computing the distance function. Alternatively, from the list of corresponding peaks, M chromatograms are chosen randomly. For example, if N corresponding peaks are found, the chromatograms corresponding to every $N/M^{th}$ m/z value are selected. Alternatively, the M chromatograms can be selected from the corresponding peaks based on an intensity threshold or some other criterion.

When more than one test data set is aligned to the reference data set, each pairwise alignment can be computed based on a different set of independently-selected chromatograms.

In one embodiment of the invention, a weighting factor $W_k$ is included in the distance function, causing different chromatograms to contribute unequally. As a result, certain chromatograms tend to dominate the sum and dictate the alignment. The weighted distance function is:

$$d_{i,j} = \sum_{k=1}^{M} W_k (I_{kj}^{ref} - I_{ki}^{test})^2, \quad (2)$$

where $W_k$ is the chromatogram-dependent weighting factor. The functional form or value of the weighting factor can be determined a priori based on user knowledge of the most relevant mass ranges. Alternatively, the weighting factor can be computed based on characteristics of the data. For example, the weighting factor can be a function of one or more of the following variables: the number of peaks per chromatogram (peak number), selected by any manual or automatic method; the signal-to-noise ratio in a chromatogram; and peak threshold or intensities. Chromatograms having more peaks, higher signal-to-noise ratio, or higher peak intensities are typically weighted more than other chromatograms. Any additional variables can be included in the weighting factor. The factor can also depend on a combination of user knowledge and data values.

Figures 7A, 7B:
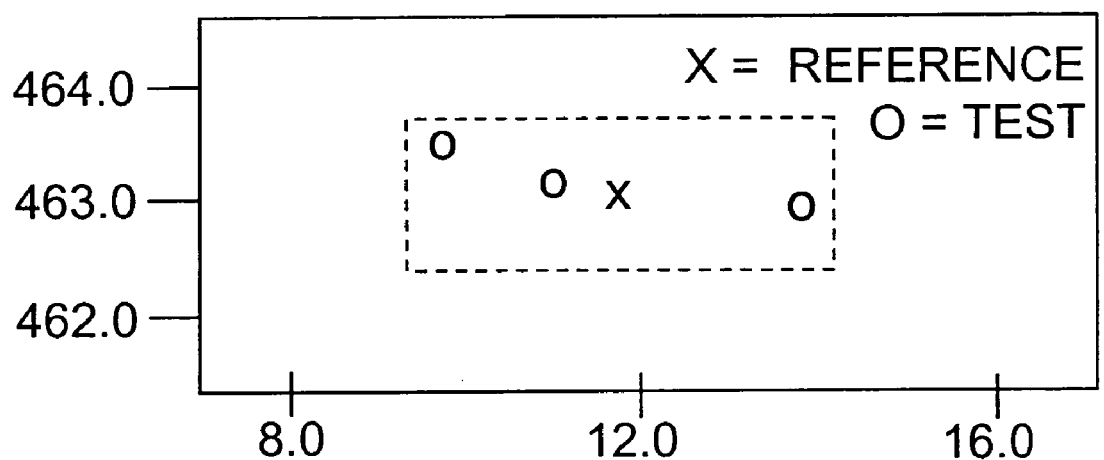
FIGS. 7A-7C illustrate aspects of a locally-weighted regression smoothing method according to one embodiment of the present invention.

In an alternative embodiment of the invention, the time-aligning step 26 employs locally-weighted regression smoothing. Rather than act on the raw (or preprocessed) data, this method time-aligns selected peaks in test and reference data sets. Peaks, defined by m/z and retention time values, are first selected from each data set by manual or automatic means. Potentially corresponding peaks are identified from the lists as peaks that fall within a specified range of m/z and retention time values. FIG. 7A shows an excerpt of a reference peak list and test peak list with potentially corresponding peaks shaded. These peaks are plotted in FIG. 7B, which shows the window surrounding the reference peak that defines a region of potentially corresponding test peaks. Because the nonlinear time variations have not yet been corrected, the window has a relatively large retention time range, accounting for the maximum retention time variation throughout the chromatographic run (e.g., five minutes).

Figure 7C:
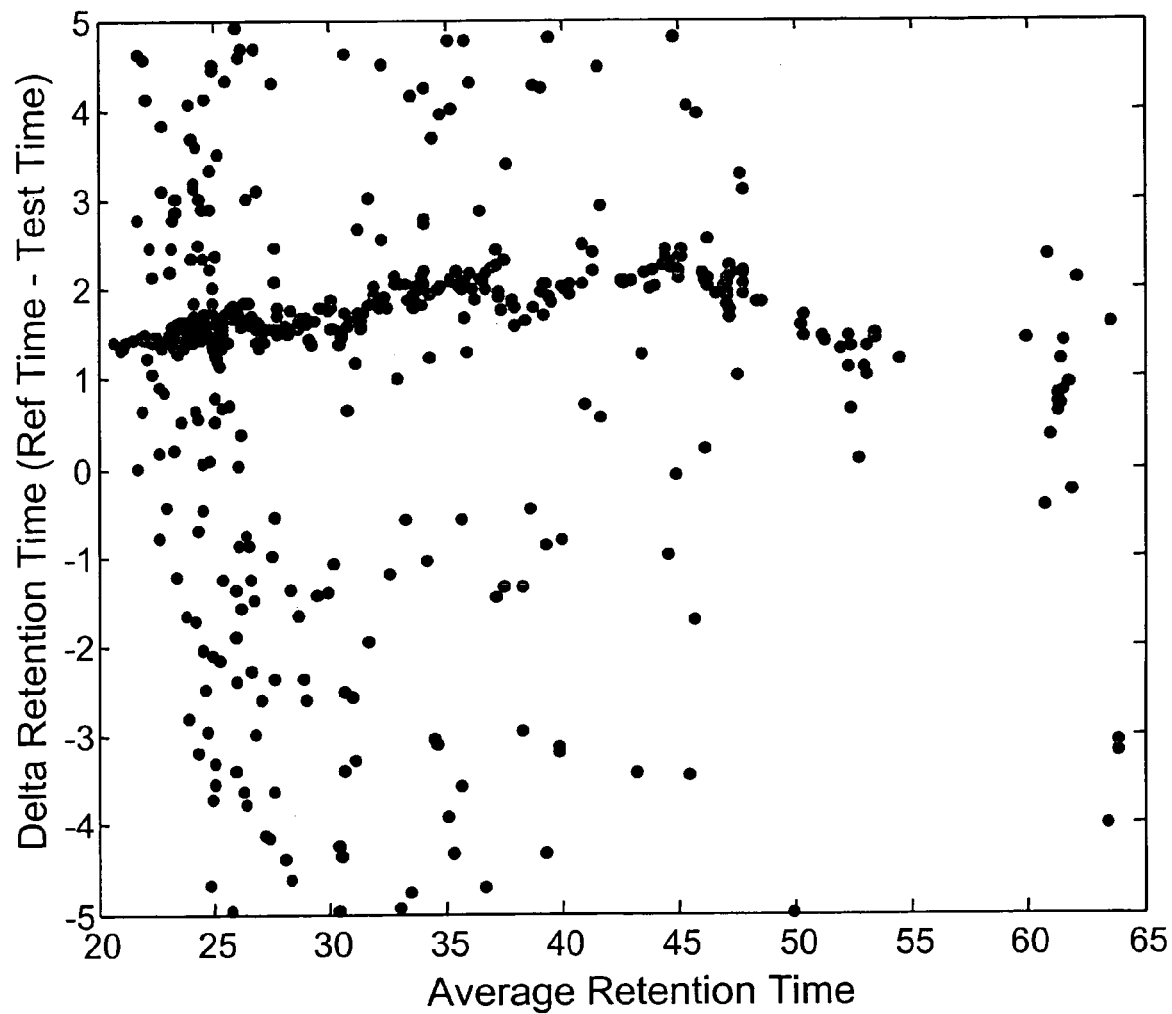

For every pair of reference peak and potentially corresponding test peak, the data are transformed from $(t_{ref}, t_{test})$ to $(t_{avg}, \Delta t)$, where $t_{avg}=(t_{ref}+t_{test})/2$ and $\Delta t=t_{ref}-t_{test}$. The resulting plot, for exemplary data sets, is shown in FIG. 7C. It is apparent from FIG. 7C that the points tend to cluster around a curve that represents the nonlinear time variation between reference and test data sets. Knowing this curve would enable correction of the time variation and alignment of the data sets.

To do so, a smoothing algorithm is applied to the transformed variables to yield a set of discrete values $(t_{avg}, \Delta t)$, which can be transformed back to $(t_{ref}, t_{test})$. Because the smoothing is applied to data points representing peaks, and because the result is a discrete mapping of points rather than a function, adjusted time values of data points between the peaks are then computed, e.g., by interpolation. After all points have been mapped, aligned data sets can be constructed. Typically, time points of the reference data set are fixed and the test data set modified. This process can be repeated to align all data sets to the reference data set.

One suitable smoothing algorithm is a LOESS algorithm (locally weighted scatterplot smooth), originally proposed in W. S. Cleveland, "Robust locally weighted regression and smoothing scatterplots," *J. Am. Stat. Assoc.* 74: 829-836, 1979, and further developed in W. S. Cleveland and S. J. Devlin, "Locally weighted regression: an approach to regression analysis by local fitting," *J. Am. Stat. Assoc.* 83: 596-610, 1988, both of which are incorporated herein by reference. A LOESS function (sometimes called LOWESS) is available in many commercial mathematics and statistics software packages such as S-PLUS®, SAS, Mathematica, and MATLAB®.

The LOESS method, described in more detail below, fits a polynomial locally to points in a window centered on a given point to be smoothed. Both the window size ("span") and polynomial degree must be selected. The span is typically specified as a percentage of the total number of points. In standard LOESS, a polynomial is fit to the span by weighting points in the window based on their distance from the point to be smoothed. After fitting the polynomial, the smoothed point is replaced by the computed point, and the method proceeds to the next point, recalculating weights and fitting a new polynomial. Each time, even though the entire span is fit by the polynomial, only the center point is adjusted. Because the method operates locally, it is quite effective at representing the fine nonlinear variations in chromatographic retention time.

A robust version of LOESS, which is more resistant to outliers, computes the smoothed points in an iterative fashion by continuing to modify the weights until convergence (or based on a selected number of iterations). The iterative corrections are based on the residuals between the polynomial fit and the raw data points. After the points are fit using initial weights, subsequent weights are computed as the products of the initial weights and the new weights. Upon convergence, the span is moved by one point and the entire process repeated. In this manner, the polynomial regression weights are based on both the distance from the point to be smoothed (distance in abscissa value) and the distance between the point and the curve fit (distance in ordinal value), yielding a very robust fit.

Specific details of the robust LOESS fit are described below. It is to be understood that any variations in parameters, weighting factors, and polynomial degree are within the scope of the present invention. Each discrete $(t_{avg}^i, \Delta t^i)$ point is represented in the formulae below as $(x_i, y_i)$. The approximated value of $y_i$ computed from the polynomial fit is represented as $\hat{y}_i$.

First, a window size is chosen and centered on the point to be smoothed, x. Suitable window sizes are between about 10% and about 50% (e.g., about 30%) of the total span of $x_i$ values. The results may be sensitive to the span, and the optimal span depends on a number of factors, including the threshold by which peaks are selected. For example, if the peak selection threshold is low, yielding a large number of densely located points, the optimal span size may be larger than if the peak selection threshold were to yield fewer, less dense points. The span can also be selected by performing the smoothing using a few different spans and selecting the one that yields the best alignment according to a fit metric, a measure of how well the smoothed values fit the apparent alignment function or of how much the Δt value varies locally or globally across the retention time range. The smoothing can also be evaluated based on knowledge of the expected result. The N points within the chosen span are fit to a weighted polynomial of degree L (typically, L=2) by minimizing the regression merit function, $\chi^2$:

$$\chi^2 = \sum_{i=1}^{N} w_i \left[ y_i - \sum_{k=0}^{L} a_k x_i^k \right]^2, \quad (5)$$

where $a_k$ are the polynomial coefficients to be solved for and $w_i$ are the regression weights for each point $x_i$ in the span. Initially, the weights $w_i$ are given by a tricubic function:

$$w_i^{initial} = \left(1 - \left|\frac{x - x_i}{x - x_{max}}\right|^3\right)^3, \quad (6)$$

where x is the point being smoothed, $x_i$ are the individual points within the span, and $x_{max}$ is the point farthest from x. The weights vary smoothly from 0 for the point farthest from the smoothed point to 1 for the smoothed point. All weights are zero for points outside the span. The regression merit function in equation (5) is minimized to determine the polynomial coefficients $a_k$. For standard LOESS, the smoothed value ŷ is computed from the polynomial, and the span is moved one point to the right to smooth the next point.

For robust LOESS, these results are used to compute the robust weights based on the residual $r_i$ between the raw data value $y_i$ and polynomial value $ŷ_i$ for each point in the span:

$$r_i = y_i - ŷ_i, \quad (7)$$

and on the median absolute deviation MAD:

$$MAD = median(|r_i|). \quad (8)$$

From these, the robust weights $w_i^{robust}$ are computed:

$$w_i^{robust} = \begin{cases} 1 - \left(\frac{r_i}{6 \, MAD}\right)^2 & |r_i| < 6 \, MAD \\ 0 & |r_i| \geq 6 \, MAD \end{cases} \quad (8)$$

The regression is performed again for the span (from equation (5)) using newly computed weights $w_i = w_i^{initial} * w_i^{robust}$ bust to obtain a new curve fit, a new set of points $ŷ_i$, and new residuals $r_i$. This procedure (computing robust weights and fitting the polynomial) is repeated until the curve fit converges to a desired precision or for a predetermined number of iterations, e.g., about 5. Upon convergence, the y value of the point being smoothed, x, is replaced with the curve fit value. Only that point is replaced—all other points in the span remain the same. The span is then shifted one point to the right and the entire procedure repeated to smooth the point in the center of the span. Each time the curve fit is performed, the $y_i$ values used are the raw data values, not the smoothed ones. End points are treated as is commonly done in smoothing.

After all $ŷ_i$ values are obtained, a mapping from $t_{ref}$ to $t_{test}$ is determined, and values for intermediate points are computed by interpolation. The retention time values of mapped test points are then adjusted to align the complete data sets. The process is repeated for all test data sets. Note that if the goal of the method is to align corresponding peaks only, it is not necessary to find aligned time point values for the intermediate points.

Although not limited to any particular hardware configuration, the present invention is typically implemented in software by a system containing a computer that obtains data sets from an analytical instrument (e.g., LC-MS instrument) or other source. The LC-MS instrument includes a liquid chromatography instrument connected to a mass spectrometer by an interface. The computer implementing the invention typically contains a processor, memory, data storage medium, display, and input device (e.g., keyboard and mouse). Methods of the invention are executed by the processor under the direction of computer program code stored in the computer. Using techniques well known in the computer arts, such code is tangibly embodied within a computer program storage device accessible by the processor, e.g., within system memory or on a computer-readable storage medium such as a hard disk or CD-ROM. The methods may be implemented by any means known in the art. For example, any number of computer programming languages, such as Java™, C++, or Perl, may be used. Furthermore, various programming approaches such as procedural or object oriented may be employed. It is to be understood that the steps described above are highly simplified versions of the actual processing performed by the computer, and that methods containing additional steps or rearrangement of the steps described are within the scope of the present invention.

EXAMPLES

The following examples are provided solely to illustrate various embodiments of the present invention and are not intended to limit the scope of the invention to the disclosed details.

Example 1

Peaks Aligned by Dynamic Time Warping

Pooled human serum from blood bank samples was ultrafiltered through a 10-kDa membrane, and the resulting high-molecular weight fraction was reduced with dithiothreitol (DTT) and carboxymethylated with iodoacetic acid/NaOH before being digested with trypsin. Digested samples were analyzed on a binary HP 1100 series HPLC coupled directly to a Micromass (Manchester, UK) LCT™ electrospray ionization (ESI) time-of-flight (TOF) mass spectrometer equipped with a microspray source. PicoFrit™ fused-silica capillary columns (5 μm BioBasic $C_{18}$, 75 μm×10 cm, New Objective, Woburn, Mass.) were run at a flow rate of 300 nL/min after flow splitting. An on-line trapping cartridge (Peptide CapTrap, Michrom Bioresources, Auburn, Calif.) allowed fast loading onto the capillary colunm. Injection volume was 20 μL. Gradient elution was achieved using 100% solvent A (0.1% formic acid in water) to 40% solvent B (0.1% formic acid in acetonitrile) over 100 min.

Data sets were aligned by dynamic time warping (DTW) implemented in MATLAB® (The MathWorks, Cambridge, Mass.) with custom code.

Figure 8A:
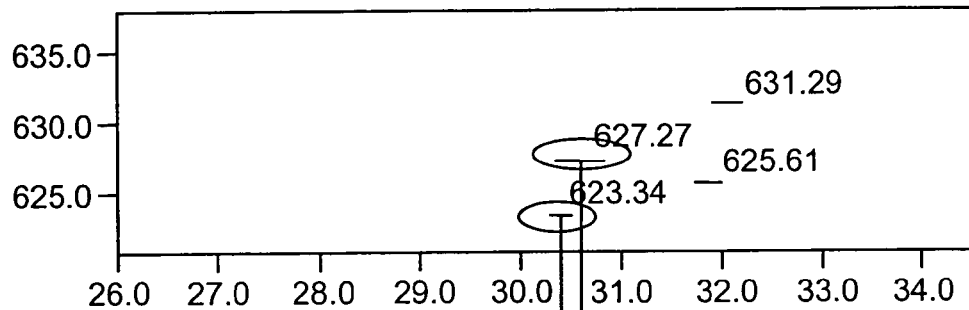
FIGS. 8A-8B show corresponding peaks of one reference and three test LC-MS data sets before and after time-alignment by DTW.
Figure 8A:
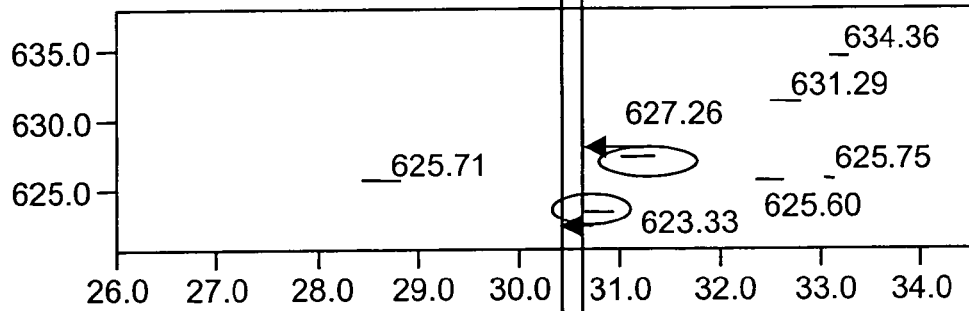
Figure 8A:
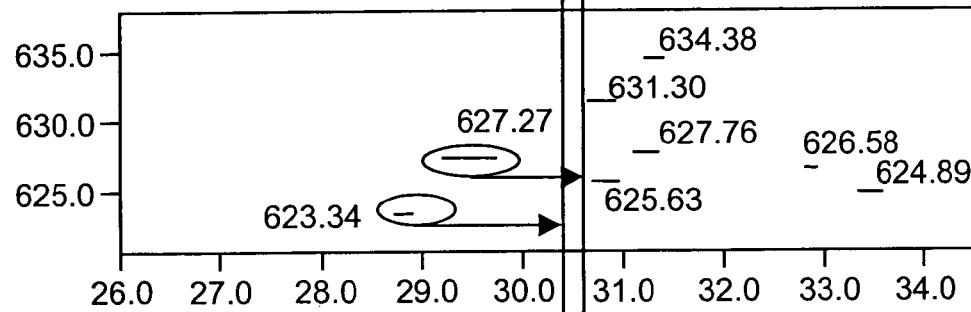
Figure 8A:
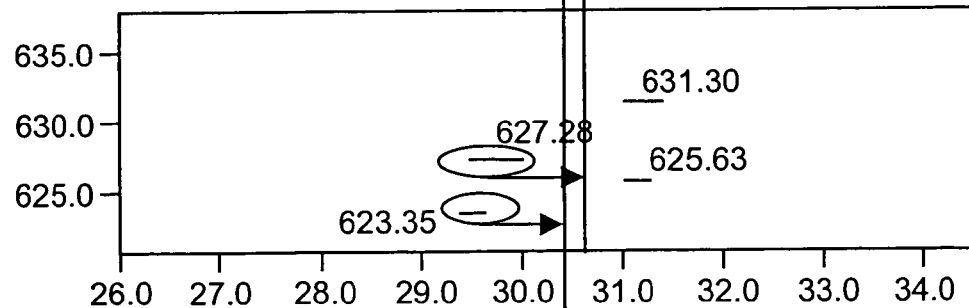
Figure 8B:
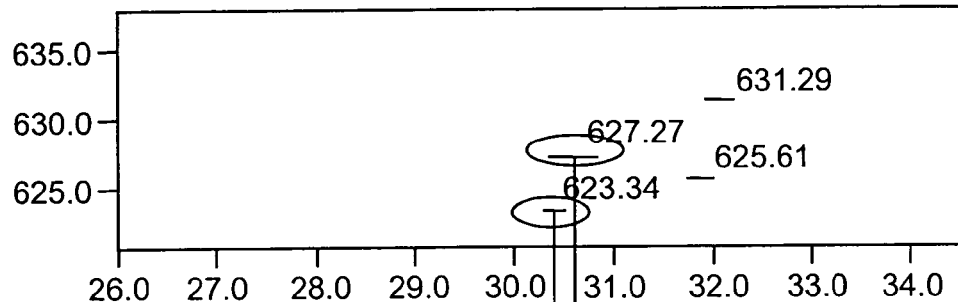
Figure 8B:
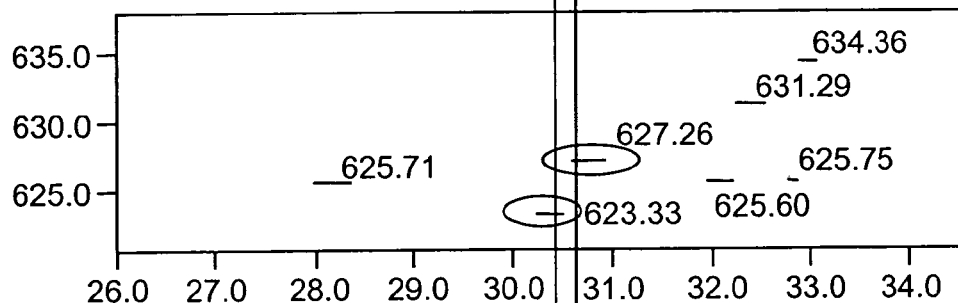
Figure 8B:
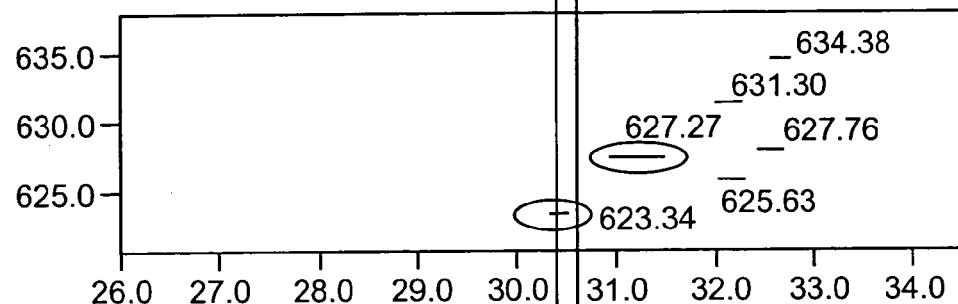
Figure 8B:
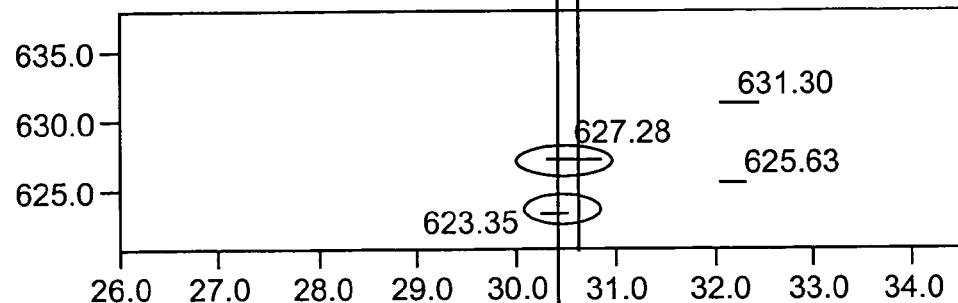

FIGS. 8A-8B show a small region of data sets corresponding to four different samples, before and after alignment of the bottom three data sets (test) to the top (reference) data set using DTW. Corresponding peaks are indicated. In all cases, the aligned peaks are much closer (in retention time) to the reference peaks than they were before alignment.

Example 2

Data Sets Aligned by Dynamic Time Warping and LOESS

Pooled human serum from blood bank samples was ultrafiltered through a 10-kDa membrane, and the resulting high-molecular weight fraction was reduced with dithiothreitol (DTT) and carboxymethylated with iodoacetic acid/NaOH before being digested with trypsin. Digested samples were analyzed on a binary HP 1100 series HPLC coupled directly to a ThermoFinnigan (San Jose, Calif.) LCQ DECA™ electrospray ionization (ESI) ion-trap mass spectrometer using automatic gain control. PicoFrit™ fused-silica capillary columns (5 µm BioBasic $C_{18}$, 75 µm×10 cm, New Objective, Woburn, Mass.) were run at a flow rate of 300 nL/min after flow splitting. An on-line trapping cartridge (Peptide Cap-Trap, Michrom Bioresources, Auburn, Calif.) allowed fast loading onto the capillary column. Injection volume was 20 µL. Gradient elution was achieved using 100% solvent A (0.1% formic acid in water) to 40% solvent B (0.1% formic acid in acetonitrile) over 100 min.

Spectra were aligned using both dynamic time warping (DTW) and robust LOESS. Algorithms were implemented in MATLAB® (The MathWorks, Cambridge, Mass.). Robust LOESS smoothing was performed using a prepackaged routine in the MATLAB® Curve Fitting Toolbox. DTW was implemented with custom MATLAB® code following the algorithms described above.

Figure 9:
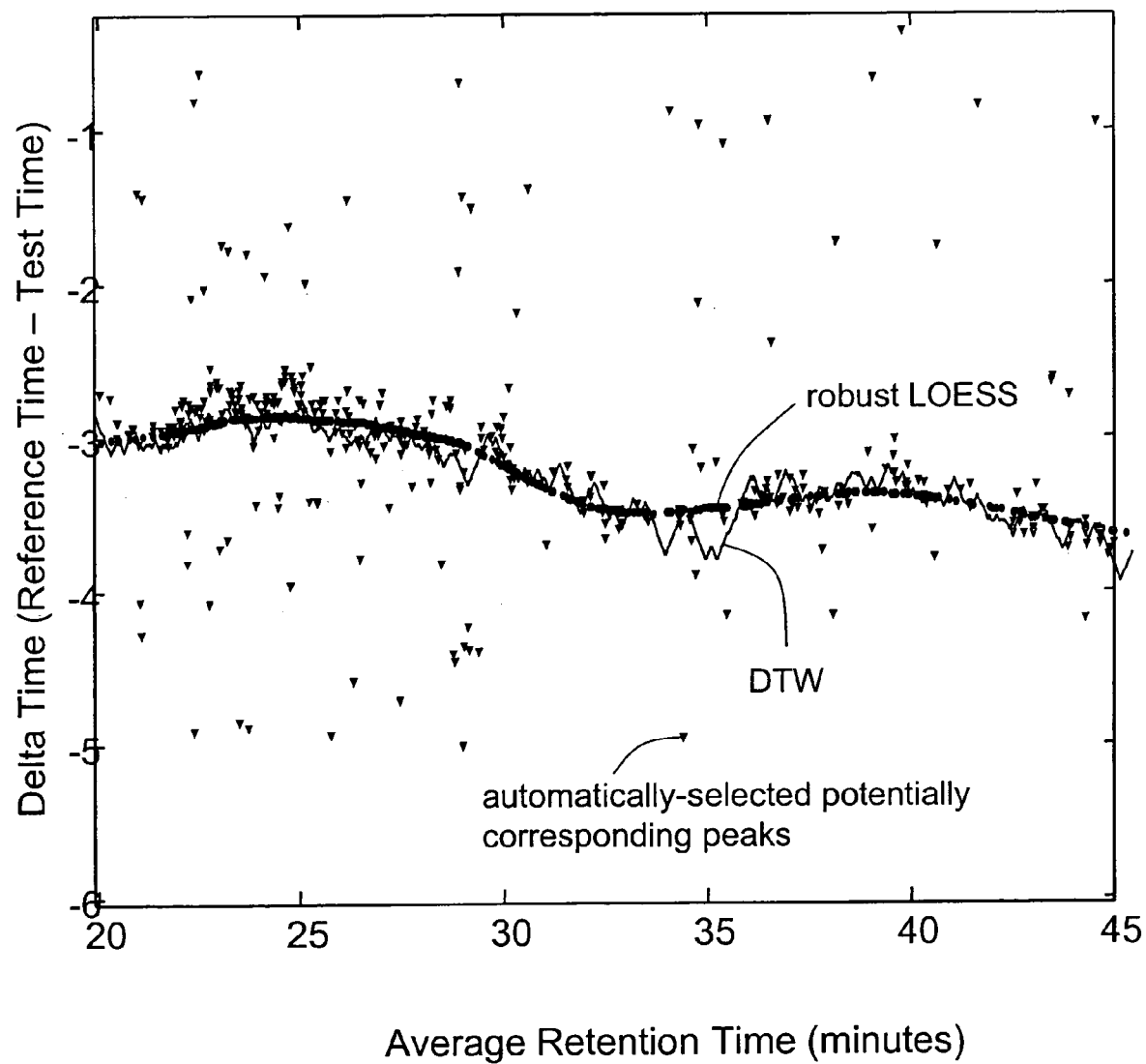
FIG. 9 is a plot showing results of alignment of LC-MS data sets by robust LOESS and DTW.

FIG. 9 is a plot of transformed data set variables $\Delta t$ vs. $t_{avg}$ showing alignment by robust LOESS and DTW. Inverted triangles represent potentially corresponding automatically-selected peaks, filled circles are points smoothed by robust LOESS, and the thin solid line is the data set corrected by DTW. The DTW points are much more densely spaced, because they are taken from the entire data set, rather than selected peaks only. In this example, both robust LOESS and DTW accurately track the time shift, with LOESS following the local variations more closely.

It should be noted that the foregoing description is only illustrative of the invention. Various alternatives and modifications can be devised by those skilled in the art without departing from the invention. Accordingly, the present invention is intended to embrace all such alternatives, modifications and variances which fall within the scope of the disclosed invention.

What is claimed is:

1. A program storage device accessible by a processor, tangibly embodying a program of instructions executable by said processor to perform method steps for a method for time-aligning chromatography-mass spectrometry data sets, each comprising a plurality of mass chromatograms, said method steps comprising:
   a) receiving data generated by a mass spectrometer;
   b) computing a distance function between said data sets in dependence on at least two mass chromatograms from each data set; and
   c) aligning said data sets by minimizing said distance function to obtain aligned data sets.

2. A program storage device accessible by a processor, tangibly embodying a program of instructions executable by said processor to perform method steps for a method for time-aligning two-dimensional chromatography-mass spectrometry data sets, said method steps comprising:
   a) receiving data generated by a mass spectrometer;
   b) selecting peaks in said data sets;
   c) identifying potentially corresponding peaks from said selected peaks; and
   d) performing a locally-weighted regression smoothing on said potentially corresponding peaks to obtain aligned data sets.

3. The program storage device of claim 2, wherein the step of selecting of peaks is performed automatically.

4. The program storage device of claim 2, wherein one of said data sets is a reference data set and one of said data sets is a test data set, and wherein said test data set is aligned to said reference data set.

5. The program storage device of claim 2, wherein said data sets are liquid chromatography-mass spectrometry data sets.

6. The program storage device of claim 2, wherein the step of performing said locally-weighted regression smoothing is a robust locally-weighted regression smoothing.

7. The program storage device of claim 6, wherein said robust locally-weighted regression smoothing comprises robust LOESS.

8. The program storage device of claim 2, wherein the said step of performing said locally-weighted regression smoothing is performed in dependence on a span.

* * * * *